United States Patent
Merz

(10) Patent No.: US 10,420,911 B2
(45) Date of Patent: Sep. 24, 2019

(54) APPARATUS FOR ASCERTAINING A PERSONAL TINNITUS FREQUENCY

(71) Applicant: RESAPHENE SUISSE AG, Roggwil TG (CH)

(72) Inventor: Volker Merz, Trossingen (DE)

(73) Assignee: Resaphene Suisse AG, Roggwil TG (CH)

( * ) Notice: Subject to any disclaimer, the term of this patent is extended or adjusted under 35 U.S.C. 154(b) by 268 days.

(21) Appl. No.: 15/049,325

(22) Filed: Feb. 22, 2016

(65) Prior Publication Data
US 2016/0250440 A1    Sep. 1, 2016

(30) Foreign Application Priority Data
Feb. 27, 2015 (DE) .................. 10 2015 102 875

(51) Int. Cl.
| | | |
|---|---|---|
| *A61M 21/00* | (2006.01) | |
| *H04R 25/00* | (2006.01) | |
| *A61B 5/12* | (2006.01) | |
| *H04R 1/10* | (2006.01) | |
| *H04R 3/04* | (2006.01) | |
| *A61B 5/00* | (2006.01) | |

(52) U.S. Cl.
CPC ............. *A61M 21/00* (2013.01); *A61B 5/128* (2013.01); *A61B 5/6803* (2013.01); *A61B 5/6817* (2013.01); *H04R 1/1083* (2013.01); *H04R 1/1091* (2013.01); *H04R 3/04* (2013.01); *H04R 25/552* (2013.01); *H04R 25/75* (2013.01); *A61M 2021/0027* (2013.01); *A61M 2210/0662* (2013.01); *H04R 1/1016* (2013.01); *H04R 2420/07* (2013.01); *H04R 2420/09* (2013.01); *H04R 2460/01* (2013.01)

(58) Field of Classification Search
CPC ............ H04R 25/75; H04R 1/10–1091; H04R 25/652
See application file for complete search history.

(56) References Cited

U.S. PATENT DOCUMENTS

| | | |
|---|---|---|
| 2,344,023 A | 3/1944 | Carlisle et al. |
| 4,513,197 A | 4/1985 | Courvoisier et al. |
| | (Continued) | |

FOREIGN PATENT DOCUMENTS

| | | |
|---|---|---|
| CN | 202682155 U | 1/2013 |
| DE | 10 2010 039 589 A1 | 2/2012 |
| | (Continued) | |

OTHER PUBLICATIONS

European Search Report, European Application No. 16156415.8, dated Jul. 13, 2016 (19 pages).

(Continued)

*Primary Examiner* — Catherine B Kuhlman
(74) *Attorney, Agent, or Firm* — Burr & Brown, PLLC

(57) ABSTRACT

The present invention comprises an apparatus for ascertaining a personal tinnitus frequency consisting of an audio signal generator unit and an associated audio signal earphone, which apparatus provides a first audio signal whose frequency is continuously adjustable. The invention is characterized in that compensating means are provided in order to eliminate ambient noise through active noise reduction.

10 Claims, 4 Drawing Sheets

(56) References Cited

U.S. PATENT DOCUMENTS

| | | | |
|---|---|---|---|
| 6,741,719 B1 * | 5/2004 | Orten | A61B 7/04 381/380 |
| 7,377,666 B1 | 5/2008 | Tyler | |
| 2005/0209516 A1 * | 9/2005 | Fraden | A61B 5/02055 600/323 |
| 2009/0074219 A1 * | 3/2009 | Klemenz | H04R 25/00 381/324 |
| 2011/0051947 A1 | 3/2011 | Macours | |
| 2012/0046713 A1 | 2/2012 | Hannemann et al. | |
| 2012/0051561 A1 * | 3/2012 | Cohen | G10L 21/00 381/122 |
| 2012/0283593 A1 * | 11/2012 | Searchfield | H04R 25/75 600/559 |
| 2013/0131542 A1 * | 5/2013 | Henry | A61B 5/121 600/559 |
| 2014/0126733 A1 | 5/2014 | Gauger, Jr. et al. | |
| 2015/0038774 A1 | 2/2015 | Poulsen | |
| 2015/0245151 A1 | 8/2015 | Nötzel et al. | |
| 2016/0173971 A1 * | 6/2016 | Lott | H04R 1/1066 381/380 |
| 2016/0317352 A1 * | 11/2016 | Blumer | A61F 11/08 |

FOREIGN PATENT DOCUMENTS

| | | | |
|---|---|---|---|
| DE | 10 2012 220 620 A1 | | 5/2014 |
| KR | 20070060621 A | * | 6/2007 |
| KR | 20100078190 A | * | 7/2010 |

OTHER PUBLICATIONS

Partial European Search Report, European Application No. 16156415.8, dated Apr. 22, 2016 (6 pages).

* cited by examiner

APPARATUS FOR ASCERTAINING A PERSONAL TINNITUS FREQUENCY

This application claims the benefit under 35 USC § 119(a)-(d) of German Application No. 10 2015 102 875.1 filed Feb. 27, 2015, the entirety of which is incorporated herein by reference.

FIELD OF THE INVENTION

The present invention relates to an apparatus for ascertaining a personal tinnitus frequency, consisting of an audio signal generator unit and an associated audio signal earphone, which apparatus provides a first audio signal whose frequency is continuously adjustable.

BACKGROUND OF THE INVENTION

Apparatuses for ascertaining a personal tinnitus frequency are known and are used in medical practices, for example, in rooms provided specifically for the purpose that are acoustically isolated from ambient noise, that is to say in a quiet environment, for ascertaining a personal tinnitus.

A disadvantage of these apparatuses is the distance and the associated time to and with the doctor for the user. A further disadvantage is the ambient noise that arises as a result of poor acoustic isolation in the treatment rooms of the doctor, such as telephone ringing, which makes ascertainment and treatment of personal tinnitus with known apparatuses difficult.

SUMMARY OF THE INVENTION

The present invention is based on the object of providing an improved apparatus, for the ascertainment and treatment of personal tinnitus, for use by the tinnitus victim.

The present invention is based on an apparatus for ascertaining a personal tinnitus frequency, consisting of an audio signal generator unit and an associated audio signal earphone that provides a first audio signal whose frequency is continuously adjustable.

The essential aspect of the present invention can now be seen in that compensating means are provided in order to eliminate ambient noise through active noise reduction.

An associated audio signal earphone may be connected to the audio signal generator unit via a cable connection or even via a radio link, for example.

By way of example, a power supply unit, for example a battery or a storage battery, is arranged on an audio signal earphone.

A compensating means for the active reduction of ambient noise may be arranged on an audio signal earphone, in particular, that is embodied as what is known as a noise cancellation earphone (ANC earphone), for example.

The active reduction of ambient noise means that the tinnitus therapy device can be used in an ordinary, domestic environment as a wellness device for the treatment of tinnitus.

A user can use adjusting means, for example, which are arranged on the apparatus, to continuously alter a frequency and/or a phase of the frequency and/or if need be an amplitude of a played first audio signal and thereby determine his personal tinnitus frequency and if need be the phase of the personal tinnitus frequency and possibly the amplitude of the personal tinnitus frequency himself in a domestic environment.

Adjusting means are understood to mean, inter alfa, by way of example, rotary controls, slide controls, control knobs, rotary knobs, toggle switches, pressure switches or else contactless operating control elements, which are operated by gestures, particularly by voice, for example.

It is also conceivable for a frequency and/or a phase of the frequency and/or an amplitude of a played first audio signal to be adjustable for each ear separately using an adjusting means on the apparatus for ascertaining a personal tinnitus frequency.

The ascertained personal tinnitus frequency and if need be the ascertained phase of the personal tinnitus frequency and possibly the amplitude of the personal tinnitus frequency can be stored on the apparatus for ascertaining a personal tinnitus frequency. By way of example, on a memory unit—not defined further—that is arranged on the apparatus for ascertaining a personal tinnitus frequency. Additionally arranged adjusting means can be used to store the information particularly in recallable form.

It is also conceivable for a user to be able to store a personal tinnitus frequency that has previously been ascertained otherwise and/or at a different time and/or at a different location and/or using a different apparatus, and/or if need be the ascertained phase of the personal tinnitus frequency and/or possibly the amplitude of the personal tinnitus frequency, in recallable form on a memory unit—not defined further—on the apparatus for ascertaining a personal tinnitus frequency.

A further essential aspect of the present invention lies in that a heating arrangement for heating an ear region is provided on the apparatus. The heating arrangement can be used in addition to the apparatus described above or independently of noise reduction.

In particular, the heating arrangement may be arranged on an audio signal earphone. By way of example, a heatable audio signal earphone can be used to stimulate the blood flow of the ear, for example, of the middle and/or inner ear.

The heatable audio signal earphone and/or the apparatus for ascertaining a personal tinnitus frequency may, by way of example, be embodied such that a temperature can be set in continuously regulatable fashion for each ear separately. Advantageously, an adjusting means for setting a temperature for a heatable earphone may be arranged on the apparatus for ascertaining a personal tinnitus frequency, for example.

It is also advantageous that an audio signal earphone is in the form of an earplug.

By virtue of an audio signal earphone being in the form of an earplug, which is referred to particularly as an in-ear earphone, for example, it is possible for the wearing comfort of the audio signal earphone to be improved.

The design of an audio signal earphone as an earplug allows individual earplug shaping to an ear geometry or outer ear canal geometry of the user and hence a comparative improvement in wearing comfort. By way of example, the earplug may have an earplug case element that encloses the earplug of the audio signal earphone and matches the individual ear geometry or outer ear canal geometry of the user.

Advantageously, the earplug case element may be formed from silicone. Silicone is a comparatively good conductor of heat, in particular, which means that it has good suitability as a material for use on an audio signal earphone with a heating arrangement, for example. As result, it is a simple matter for the ear or the outer canal of the ear to be heated.

An audio signal earphone that is in the form of an earplug can heat both the inner ear and the middle ear, for example, to different temperatures separately from one another.

In addition, it is proposed that an adjusting means arranged on the audio signal generator unit can be used to select a first and/or second audio signal.

Adjusting means that are arranged on the apparatus can provide a user with the opportunity to select a first audio signal on the tinnitus therapy device, for example. The first audio signal may be in a form such that it comes extremely close to a personal tinnitus tone, for example, a beep tone, a ringing tone, noise or a tinnitus tone formed otherwise.

The sound can also be compiled from multiple frequencies, for example. When the user alters the adjustable frequency on the apparatus for ascertaining a personal tinnitus frequency by means of an adjusting means in order to ascertain his personal tinnitus frequency, the tinnitus therapy device alters all frequencies occurring in the first audio signal, by means of an adjusting means arranged on the audio signal generator unit, as appropriate. By way of example, all frequencies occurring in the first audio signal are altered by +1 Hz when the user alters the adjustable frequency by +1 Hz by means of the adjusting means of the audio signal generator unit.

It is moreover advantageous that the apparatus has an element that can be used to continuously regulate an ascertained personal tinnitus frequency in a narrow frequency range.

By way of example, the tinnitus therapy device has an adjusting means that can be used to continuously alter the ascertained personal tinnitus frequency in a narrow frequency range around the personal tinnitus frequency.

In addition, it is proposed that the apparatus is designed to produce a second audio signal, in which an ascertained personal tinnitus frequency has been altered.

A second audio signal, which can be played on an audio signal earphone and which is stored in recallable form and selectable in a memory unit—not defined in more detail—of the apparatus for ascertaining a personal tinnitus frequency or an external memory unit, can be altered by means of an audio element, which is arranged on the audio signal generator unit, such that an ascertained personal tinnitus frequency is altered.

The second audio signal can comprise a tone, a sound or even a piece of music or a melody, for example.

By way of example, an ascertained personal tinnitus frequency can be filtered out of the second audio signal by an audio element, for example, the second audio signal contains only frequencies that the ascertained personal tinnitus tone does not contain.

In addition, it is conceivable for the second audio signal to be superimposed on the first audio signal by an audio element. This allows a user to perceive e.g. a pleasant second audio signal, for example (relaxation) music or pleasant sounds (birds' twittering, the rush of a stream), and unconsciously the comparatively unpleasant first audio signal. This can allow the user to be conditioned such that the user blocks out his unpleasant tinnitus tone, or does not perceive it as unpleasant, in everyday life.

It is also conceivable for an audio element, at the location or in the range of an ascertained personal tinnitus frequency in a second audio signal, to perform a phase shift in relation to a defined phase of an ascertained personal tinnitus frequency in a first audio signal.

By way of example, in one mode of the second audio signal, the phase at the tinnitus frequency of the second audio signal may have a phase shift of precisely 180° in relation to the defined phase of the personal tinnitus frequency of the first audio signal. When the phases are destructively superimposed, they can cancel one another out. With a phase shift of less than 180°, partial cancellation may take place.

It is also conceivable for, in a further mode of the second audio signal, the two phases to be precisely in phase, for example, and for the personal tinnitus frequency or the personal tinnitus frequency range therefore to be constructively superimposed and to be amplified.

Furthermore, in a further mode of the second audio signal, the phase of the ascertained personal tinnitus frequency in the second audio signal may be continuously alterable using an adjusting means on the apparatus for ascertaining a personal tinnitus frequency.

In particular, it may be conceivable for frequencies in a second audio signal to be alterable, in a further mode of the second audio signal, in a narrowband range around the ascertained personal tinnitus frequency using an adjusting means on the apparatus.

A further advantage is that an element to which a memory unit can be connected is arranged on the audio signal generator unit.

The memory unit can provide audio data for the first and/or the second audio signal, for example.

Furthermore, the memory unit may be in the form of a stick, in the form of a hard disk or in the form of a memory card, for example. The element may comprise, by way of example, a USB and/or Bluetooth and/or NFC and/or WLAN interface and/or an interface that can be used to read different memory card types.

It is also advantageous that the audio signal generator unit is constructed such that it is supplied with power by means of an external and/or internal power source.

By way of example, a power source can be connected to the apparatus for ascertaining a personal tinnitus frequency via an element that is in the form of a mini-USB connection, an inductive charging connection or a conventional mains plug connection, for example.

Furthermore, it is conceivable for a battery or a storage battery that is arranged on the apparatus for ascertaining a personal tinnitus frequency to supply the apparatus with power. By way of example, an external power source arranged with the apparatus for ascertaining a personal tinnitus frequency can be used to charge a battery or a storage battery that is arranged on the apparatus.

It may be advantageous for an indicator unit to be arranged on the audio signal generator unit.

An indicator unit, for example a display, can indicate particularly an adjustable tinnitus frequency and/or a volume, or an amplitude of the adjustable tinnitus frequency and/or a temperature and/or a second audio signal mode and/or a name of an audio file for a first and/or second audio signal.

The indicator unit may be embodied with multiple lines and/or multiple colors, for example.

Furthermore, the indicator unit can indicate, by way of example, a state of charge for an arranged energy store, for example a battery or a storage battery.

Advantageously, the audio signal generator unit has an element for an audio earphone for both a first and a second audio signal arranged on it.

By way of example, it is conceivable for the apparatus for ascertaining a personal tinnitus frequency to have two audio signal earphones arranged on it simultaneously.

By way of example, it is conceivable for the apparatus to have three contact means arranged on it. A first contact means on which a first audio earphone that provides the first audio signal is arranged, and a second contact means on which a second audio earphone that provides the second audio signal is arranged. In addition, a third contact means may be arranged on the apparatus, on which, by way of example, it is possible to arrange a cable that is connected to a heating arrangement on the earphone and that is used to provide a voltage for the heating arrangement.

It is also conceivable for the apparatus to have, by way of example, a first contact means arranged on it, on which a single audio earphone that provides both the first audio signal and the second audio signal is arranged. Furthermore, a second contact means may be arranged on the apparatus, on which second contact means it is possible to arrange a cable that is connected to the heating arrangement on the earphone, and which second contact means is used to provide the voltage for the heating arrangement.

Furthermore, it is advantageous that the apparatus has, by way of example, a single contact means arranged on it that has a single audio earphone arranged on it. Both the first audio signal and the second audio signal and also the voltage for the heating arrangement on the earphone can be provided by means of the contact means, for example.

It is particularly conceivable for the apparatus to have precisely two contact means arranged on it. A first contact means that has a first audio earphone, which provides the first audio signal, arranged on it and a second contact means that has a second audio earphone, which provides the second audio signal and on which a heating arrangement is arranged, arranged on it.

A first audio signal earphone may be in the form of an earplug that is used to provide a second audio signal having an altered personal tinnitus frequency and that can also be used to heat the ear, for example.

A second audio signal earphone may be arranged over the ear or the outer ear and the second audio signal earphone arranged on the ear and may contain compensating means for noise reduction for ambient noise.

A user of the apparatus for ascertaining a personal tinnitus frequency can, by way of example, first of all arrange on the ear a first earphone that provides the second audio signal and may be in the form of an earplug and, in particular, may be heatable. Furthermore, a user can arrange on the ear, in addition to the first earphone, a second earphone that provides the second audio signal and, by way of example, is in the form of an earphone enclosing the outer ear and that comprises compensating means for active noise reduction.

Combined use of the two audio signal earphones allows comparatively better determination of the personal tinnitus frequency and/or comparatively better, or more pleasant, wellness treatment by the played second audio signal and additionally heating of a ear region, for example.

It is also advantageous that the audio signal generator unit is in the form of a mobile unit.

By way of example, the audio signal generator unit may be equipped with an internal energy store and, in terms of size, be embodied such that the audio signal generator unit can be arranged comparatively conveniently on the body of the user. This means that a high degree of freedom of movement for the user can be made possible. By way of example, the user can use the apparatus for ascertaining a personal tinnitus frequency in a domestic environment and in so doing pursue domestic activities, for example.

In a further advantageous modification, an element for a detection element is provided on the audio signal generator unit.

By way of example, the detection element may be embodied as a measuring element that is based on an optical measurement method or as a measuring element that is based on a measurement method using ultrasound.

The detection element can be used to determine a bodily function of the user of the apparatus for ascertaining a personal tinnitus frequency, such as the pulse and/or the skin resistance and/or the blood pressure and/or the breathing rate, for example.

This advantageously allows the ascertainment of feedback from the user in response to the played second audio signal.

The detection element may be arranged on a contact means on the audio signal generator unit preferably by means of a cable or via a radio link.

Advantageously, during treatment of tinnitus in a user by means of the second audio signal, the mode of the second audio signal can be regulated, in particular automatically, on the basis of the ascertained bodily functions using a regulating element arranged on the audio signal generator unit. It is furthermore conceivable for the regulating element to regulate the mode of the second audio signal on the basis of a change in the bodily function. By way of example, the frequency and/or phase and/or amplitude of the ascertained personal tinnitus frequency and/or the mode in the second audio signal can be regulated by means of a regulating element on the basis of an ascertained bodily function.

BRIEF DESCRIPTION OF THE DRAWINGS

A plurality of exemplary embodiments are explained in more detail, providing further details and advantages, with reference to schematic drawings that appear below and in which.

DETAILED DESCRIPTION OF THE INVENTION

Figure 1:
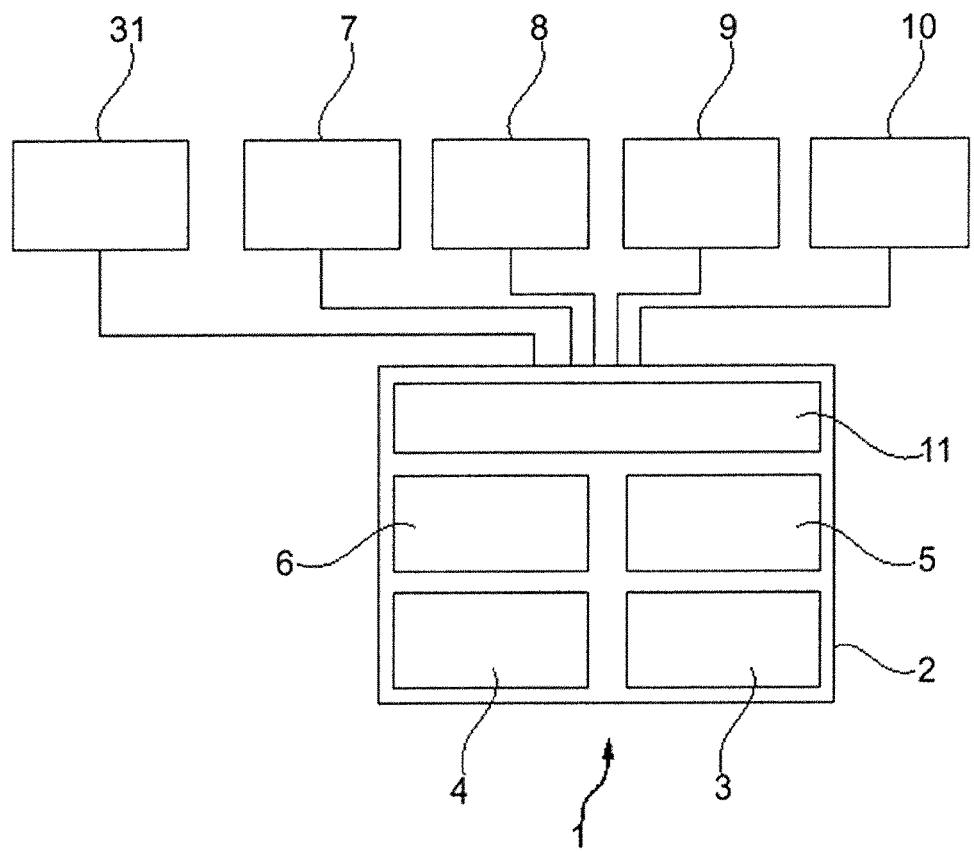
FIG. 1 shows a schematic illustration of an apparatus according to the invention.

FIG. 1 shows an apparatus 1 according to the present invention, consisting of an audio signal generator unit 2 and earphones 7, 8 arranged thereon, a mains plug 9, a memory unit 10 and a detection element 31. The audio signal generator unit 2 comprises an indicator unit 3, adjusting means 4, a regulating element 5 for adjusting audio signals, an internal energy source 6 and contact means 11 for the external earphones 7, 8, the mains plug 9, the memory unit 10 and the detection element 31.

The apparatus 1 according to the invention does not have to contain all the elements and does not have to be formed in the integrated or external embodiment shown.

Figure 2:
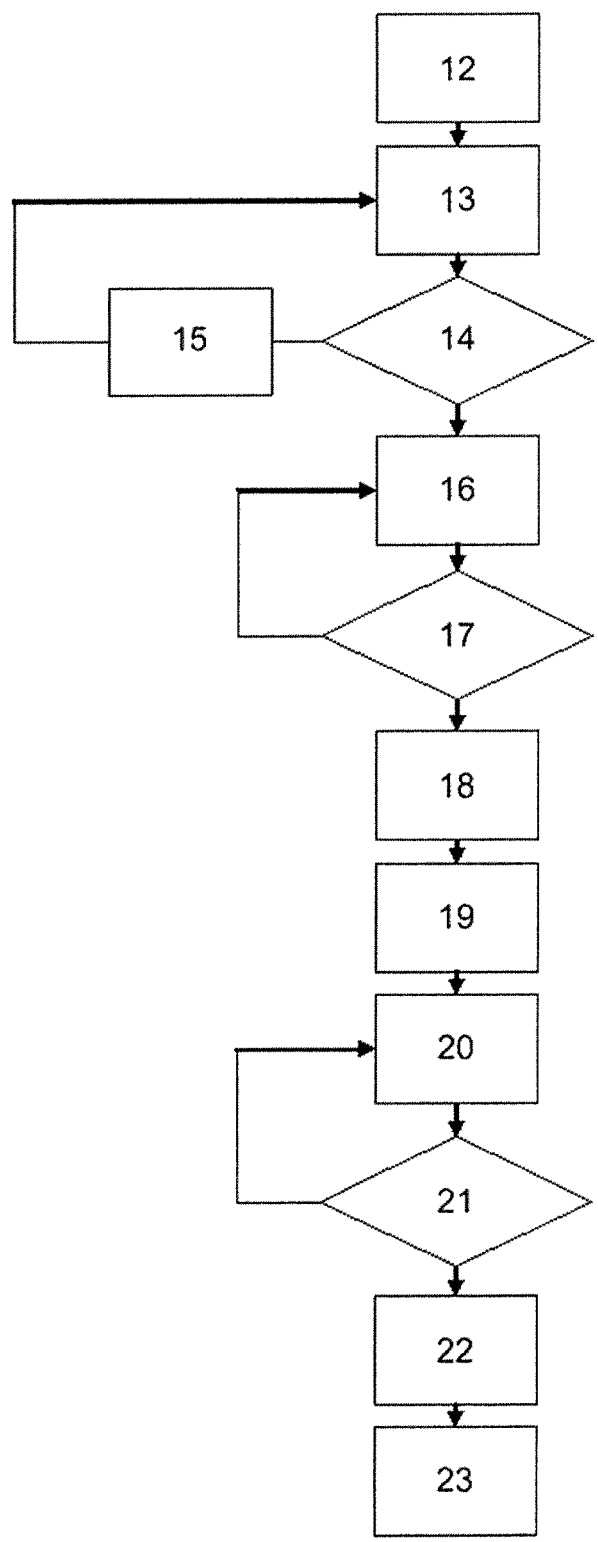
FIG. 2 shows a schematic procedure for a therapy unit by means of the apparatus according to the invention.
Figure 3:
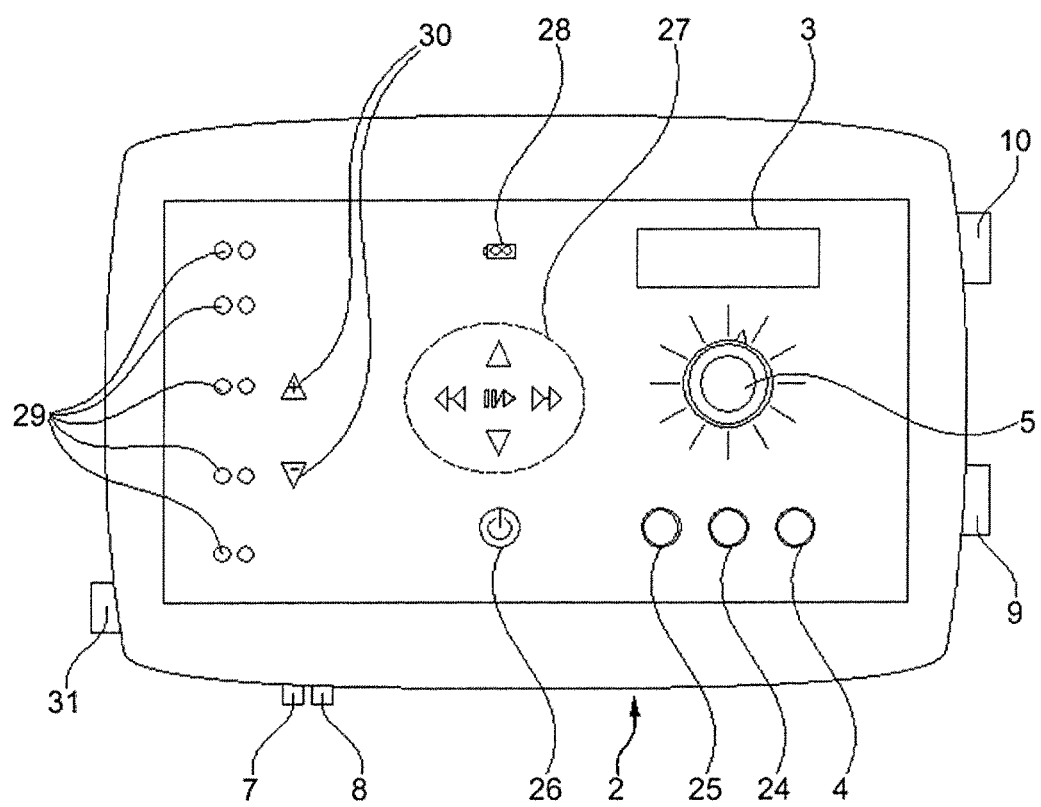
FIG. 3 shows a further schematic illustration of an audio signal generator unit of the apparatus according to the invention.

Use of the apparatus for ascertaining a personal tinnitus frequency can proceed as shown in FIG. 2, for example (in this regard see also FIGS. 1 and 3).

In a first step 12, the user 33 activates the audio signal generator unit by operating an on/off switch 26 on the audio signal generator unit 2. If need be, the user 33 additionally connects the memory unit 10 to the apparatus 1.

In a next step 13, the user 33 considers the state of charge of a battery or of a storage battery of the apparatus. The user is able to take this from the indicator unit 3 on the apparatus 1, for example.

Should the consideration in the further step 14 result in a state of charge of the apparatus 1 not being sufficient for use by the user 33, the user 33 has the opportunity firstly to connect the device to the mains plug 9, and hence to charge the device, in a further step 15 and to wait until the apparatus 1 has a sufficient state of charge in order to ensure use of the apparatus 1 over the full period of use, or secondly to connect the mains plug 9 for charging the internal energy source 6 and at the same time to continue using the apparatus at a fixed location, by virtue of the mains plug 9.

If the state of charge of the apparatus 1 is sufficient, the user 33 puts on an earphone with active noise reduction 7 in a further step 16 and then ascertains his personal tinnitus frequency without interference from ambient noise.

In an ensuing step 17, the user 33 checks the result of the ascertainment and if need be repeats step 16 until the personal tinnitus frequency has been ascertained correctly.

In a subsequent step 18, the user 33 exchanges the earphones with active noise reduction 7 for heatable in-ear earphones 8.

In a next step 19, the user 33 activates the heating of the in-ear earphones 8 to heat the ear and selects a second audio signal using adjusting means 4 on the audio signal generator unit 2 and activates said second audio signal.

In an ensuing step 20, the user 33 alters, if need be, both the volume of the second audio signal, using the adjusting means 4 on the audio signal generator unit 2, and the temperature using the adjusting means 4 on the audio signal generator unit 2.

Should a check in step 21 result in the volume and/or the temperature being unusable for the user 3, the user 33 repeats step 20.

If the volume and the temperature are pleasant for the user 33, the user 33 uses adjusting means 4, for example, in a further step 22 to select the mode in which the music or the second audio signal is intended to be activated on the audio signal generator unit 2. By way of example, the user 33 could select a mode in which the tinnitus frequency in the second audio signal is masked in a narrowband range around the personal tinnitus frequency. The user 33 could preferably choose a mode in which, by way of example, the phase of the tinnitus frequency in the second audio signal is positively (constructively) or negatively (destructively) superimposed at the location or in the range of the personal tinnitus frequency.

In a concluding step 23, the user 33 uses the adjusting means 4 to start a tinnitus therapy unit.

FIG. 3 shows a schematic illustration of the audio signal generator unit 2. The audio signal generator unit 2 can comprise an adjusting means 24 that can be used to set the volume of the first or second audio signal. In addition, the audio signal generator unit 2 can comprise an adjusting means 25 that can be used to set the mode of the tinnitus treatment. Furthermore, the audio signal generator unit 2 has a switch 26 arranged on it that can be used to switch the apparatus 1 on and off.

For the purpose of selecting the first and second audio signals, operator control elements 27 on the audio signal generator unit 2 are available to the user 33. These allow the user 33 to select the relevant audio file comparatively conveniently. Furthermore, the audio signal generator unit 2 can comprise an indicator element 28 that shows the state of charge of the external or internal energy source, for example, of the internally arranged storage battery.

In addition, the audio signal generator unit 2 may have indicator elements 29 arranged on it that are used to visually display the amplitude or the phase of the personal tinnitus frequency for the user 33. Operator control elements 30 can be used by the user 33 to vary the amplitude or phase, for example.

Figure 4:
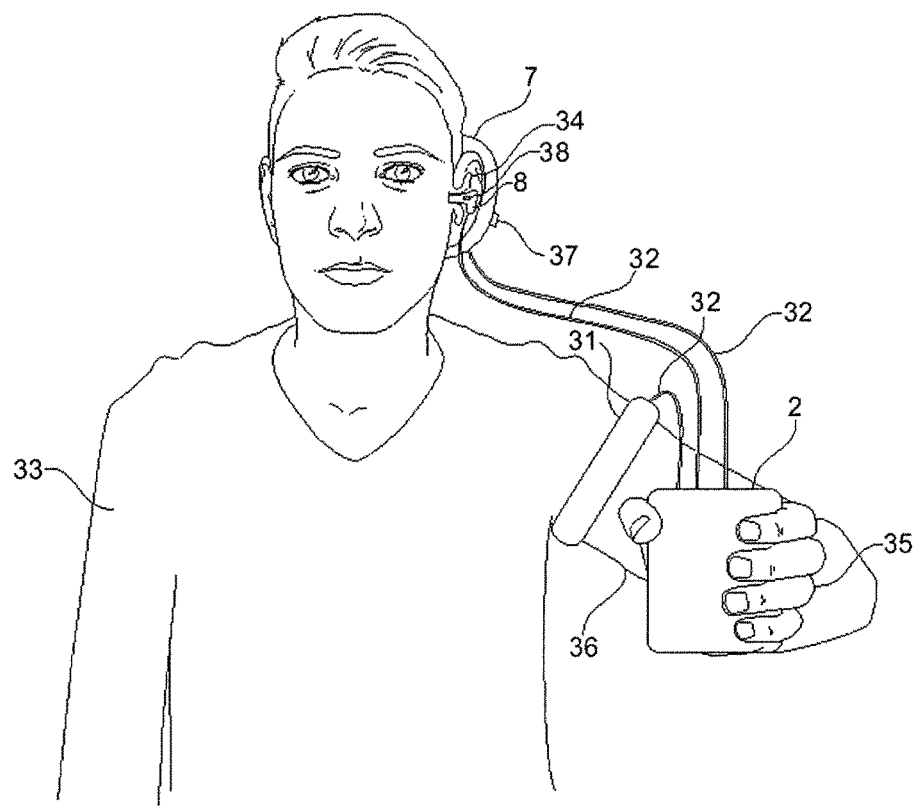
FIG. 4 shows a schematic illustration of an arrangement for the apparatus according to the invention on a user.

FIG. 4 shows the arrangement of the apparatus according to the invention on a user 33. Arranged on one ear 34 of the user 33 is an earphone 8 in the form of an earplug. This may have a heating arrangement 38 arranged on it, for example. In addition, it can reproduce the second audio signal, for example. Furthermore, an earphone 7 is arranged over the ear 34 and over the earphone 8 and is in a form such that it encloses the ear 34 completely. By way of example, the earphone 7 may have compensating means 37 for active noise reduction for ambient noise arranged on it.

The earphones 7, 8 are connected to the audio generator unit 2 by means of cables 32. The audio generator unit 2 is particularly in a form such that it can be held by the user 33 as a mobile device using one hand 35.

By way of example, the arm 36 of the user 33 furthermore has a detection element 31 arranged on it that can be used to ascertain the pulse or the blood pressure of the user 33, for example. The detection element 31 is connected to the audio generator unit 2 by means of a cable 32, for example.

LIST OF REFERENCE SYMBOLS

1 Apparatus
2 Audio signal generator unit
3 Indicator unit
4 Adjusting means
5 Regulating element
6 Energy source
7 Earphone
8 Earphone
9 Mains plug
10 Memory unit
11 Contact means
12-23 Use step
24 Adjusting means
25 Adjusting means
26 Switch
27 Operator control element
28 Indicator element
29 Indicator element
30 Operator control element
31 Detection element
32 Cable
33 User
34 Ear
35 Hand
36 Arm
37 Compensating means
38 Heating arrangement

The invention claimed is:

1. An apparatus for ascertaining a personal tinnitus frequency of a user comprising:
   an audio signal generator;
   an audio signal frequency adjuster provided on the audio signal generator;
   an associated audio signal earphone comprising at least an ear plug; and
   a heater for heating an ear region provided on the ear plug;

wherein the apparatus is configured to generate and output a first audio signal whose frequency is continuously adjustable with the audio signal frequency adjuster to tune to and thereby ascertain a personal tinnitus frequency of the user.

2. The apparatus according to claim 1, further comprising a selector for selecting the first audio signal and/or a second audio signal, arranged on the audio signal generator.

3. The apparatus according to claim 1, further comprising an adjuster for adjusting the ascertained personal tinnitus frequency in a continuously regulatable fashion over a narrow frequency range.

4. The apparatus according to claim 1, further comprising an audio element for altering the ascertained personal tinnitus frequency arranged on the signal generator, whereby the apparatus is configured to produce a second audio signal in which the ascertained personal tinnitus frequency has been altered by the audio element.

5. The apparatus according to claim 1, further comprising a memory unit connector for connecting a memory unit to the audio signal generator, arranged on the audio signal generator.

6. The apparatus according to claim 1, wherein the audio signal generator is configured to be supplied with power by an external and/or an internal power source.

7. The apparatus according to claim 1, wherein the audio signal generator is a mobile unit.

8. The apparatus according to claim 1, wherein the earphone further comprises an earphone portion surrounding the ear plug.

9. The apparatus according to claim 8, wherein in the earphone portion surrounding the ear plug further comprises compensating means to eliminate ambient noise through active noise reduction.

10. An apparatus for ascertaining a personal tinnitus frequency comprising:
an audio signal generator;
an audio signal frequency adjuster provided on the audio signal generator; and
a headphone unit including a first earphone and a second earphone;
wherein the first earphone comprises compensating means in order to eliminate ambient noise through active noise reduction;
wherein the second earphone comprises an ear plug having a heater thereon for heating an ear region; and
wherein the apparatus is configured to provide a first audio signal whose frequency is continuously adjustable with the audio signal frequency adjuster to tune to and thereby ascertain a personal tinnitus frequency of the user.

* * * * *